United States Patent [19]

Lang et al.

[11] Patent Number: 4,845,204
[45] Date of Patent: Jul. 4, 1989

[54] COSMETIC COMPOSITIONS ON THE BASIS OF ALKYL-HYDROXYPROPYL-SUBSTITUTED CHITOSAN DERIVATIVES, NEW CHITOSAN DERIVATIVES AND PROCESSES FOR THE PRODUCTION THEREOF

[75] Inventors: Günther Lang, Reinheim; Gerhard Maresch, Darmstadt; Hans-Rudi Lenz, Darmstadt; Eugen Konrad, Darmstadt; Lothar Breuer, Gross-Bieberau; Dietrich Hoch, Pfungstadt, all of Fed. Rep. of Germany

[73] Assignee: Wella Aktiengesellschaft, Darmstadt, Fed. Rep. of Germany

[21] Appl. No.: 946,576

[22] PCT Filed: Jan. 30, 1985

[86] PCT No.: PCT/EP86/00041

§ 371 Date: Oct. 3, 1986

§ 102(e) Date: Oct. 3, 1986

[87] PCT Pub. No.: WO86/04590

PCT Pub. Date: Aug. 14, 1986

[30] Foreign Application Priority Data

Feb. 7, 1985 [DE] Fed. Rep. of Germany ....... 3504095

[51] Int. Cl.$^4$ .................. C08B 37/08; A61K 7/06; A61K 7/48

[52] U.S. Cl. ..................... 536/20; 514/55; 514/844; 424/47; 424/70; 424/71; 424/401; 424/DIG. 1; 424/DIG. 2

[58] Field of Search ............... 514/55, 844; 536/20; 424/47, 70, DIG. 1, DIG. 2, 401, 71

[56] References Cited

U.S. PATENT DOCUMENTS 3,879,376  4/1975  Vanlerberghe et al. ............ 514/846
4,528,283  7/1985  Lang et al. ............................. 536/20

FOREIGN PATENT DOCUMENTS 28126  4/1981  European Pat. Off. .
97229  1/1984  European Pat. Off. .
57-180602  11/1982  Japan .

OTHER PUBLICATIONS

Chem. Abstracts, vol. 98, No. 22, May 22, 1983 abstract 181486e.
Bull. Chem. Soc. of Japan, Band 26, Nr. Apr. 3, 1953, R. Senzyu: "Untersuchungen über Lignin und Zellstoff. II. Eine neue Bestimmungsmethode des Lignins in Hölzern und Zellstoffen durch Kolloidtitration", Seiten 148–153, siehe Seite 148, Versuchsteil.

Primary Examiner—Ronald W. Griffin
Attorney, Agent, or Firm—Michael J. Striker

[57] ABSTRACT

New alkyl-hydroxypropyl-chitosans of the formula I

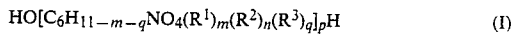
(I)

(m=0–0.6; n=0.5–10; q=0.5–4; p=50–5000; R$^1$=acetyl;

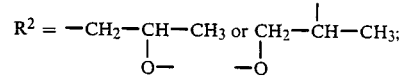

R$^3$=C$_1$–C$_6$-alkyl) and their salts with organic or inorganic acids. The invention is directed, in addition, to a process for producing the chitosan derivatives of the formula I, as well as cosmetic compositions for the treatment of hair or skin, particularly compositions for strengthening hair, comprising a content of these chitosan derivatives. The described alkyl-hydroxypropyl-chitosans are distinguished by their favorable solubility in organic solvents. Therefore, they can also be used, for example, in anhydrous hairsprays.

14 Claims, No Drawings

COSMETIC COMPOSITIONS ON THE BASIS OF ALKYL-HYDROXYPROPYL-SUBSTITUTED CHITOSAN DERIVATIVES, NEW CHITOSAN DERIVATIVES AND PROCESSES FOR THE PRODUCTION THEREOF

The invention is directed to cosmetic compositions for the treatment of hair, particularly compositions for strengthening the hairstyle, or the skin, comprising a content of new macromolecular compounds derived from chitosan in a suitable cosmetic base.

The invention is directed, further, to the new chitosan derivatives and to processes for the production thereof.

The hair and hairstyle strengtheners currently found on the market usually contain synthetic resins, which can possibly be washed out, such as polyvinyl pyrrolidone, copolymers of vinyl pyrrolidone with vinyl acetate, terpolymers of vinyl acetate with other monomers, polyacrylates and polymethacrylates and their copolymers with other monomers.

When used in hairspray recipes, the above polymers have various disadvantages. Thus, the solvents often remain for a very long time in the resin film applied to the hair, so that a relatively long drying time is necessary, and the hair feels sticky immediately after spraying on the hairspray.

In addition, the use of most of these polymers leads to a substantial interlacing of the surface of the hairstyle (so-called helmet formation), which gives the hair an unnatural appearance and a rough feel.

In addition, with most of the aforementioned polymers the ability to comb out the hair after application is considerably impaired, and the hairstyling is very difficult because of excessive electrostatic charge.

In recent times, halogen-containing propellant gases have been increasingly replaced by those that are halogen-free for ecological reasons. However, it has been established that the majority of the mentioned polymers are not suited for this purpose. Thus, precipitation of the polymers can occur during storage so that the sprays are unusable.

It has already been attempted to overcome the aforementioned disadvantages by using water soluble salts of chitosan, a polyglucosamine producible by means of deacetylation of chitin, in such cosmetic compositions. In this connection, reference is made to the present author's patents EP-PS 0 002 506 and DE-PS 2 627 419.

However, the chitosan is insoluble in anhydrous preparations, such as in anhydrous aerosol hairsprays on the basis of organic solvents in particular, and can therefore not be used in the latter. Another disadvantage of the chitosan consists in that it is insoluble in neutral or alkaline hydrous solution, so that it is not possible to apply it, for example, in alkaline permanent wave agents or hair coloring agents.

Chitosan derivatives which are soluble in organic solvents are not mentioned in the literature on the subject with very few exceptions (see, e.g. Fujii et al., Carbohydr. Res. 83, pages 389–393 (1980)).

It has now been found that chitosan can be reacted in a simple manner in mixed ether derivatives with interesting characteristics by means of two alkylation steps which are carried out one after the other or simultaneously.

The N-hydroxypropylation necessary for this purpose and the subsequent O-alkylation lead to modified, natural polymers which are distinguished particularly by their favorable solubility in organic solvents, in addition to their water solubility in the acid pH range. Accordingly, the subject matter of the invention consists in new macromolecular, polymeric compounds derived from chitosan which are obtained in this manner and have the general formula I $$HO[C_6H_{11-m-q}NO_4(R^1)_m(R^2)_n(R^3)_q]_pH \qquad (I),$$

wherein m denotes any desired numerical value from 0 to 0.6, n denotes any desired numerical value from 0.5 to 10, q is a desired numerical value from 0.5 to 4.0, p denotes an integer from 50 to 5000, $R^1$ designates an acetyl group, $R^2$ denotes a bivalent group

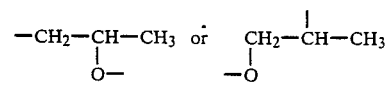

and $R^3$ denotes a straight-chain or branched alkyl radical with 1 to 6 carbon atoms, or their salts with an organic or inorganic acid.

The expression in brackets in formula I shows repeatedly substituted glucosamine monomer units.

In formula I the symbols n and q preferably have the meaning, n=1 to 3 and q=1 to 3.6, while the limiting viscosity number of the chitosan derivatives is preferably in the range of 14 to 44 ml/g.

Of the chitosan derivatives defined by the preceding general formula, the compounds particularly preferred are those constructed from 4 to 50 mole % units of the general formula

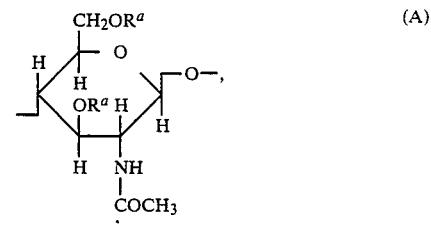

40 to 96 mole % units of the general formula

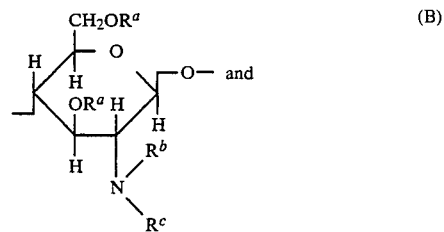

0 to 10 mole % units of the general formula

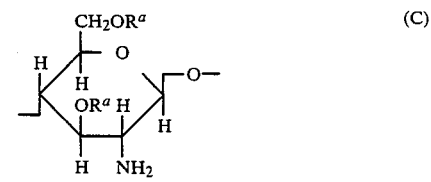

in random distribution, wherein $R^a$ denotes H or $C_1$-$C_6$-alkyl, $R^b$ is H or

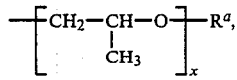

with x=an integer from 1 to 5, and $R^c$ denotes

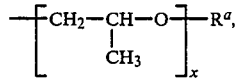

assuming that at least one of the substituents $R^a$ in formula A or B denotes $C_1$-$C_6$-alkyl.

The alkyl-hydroxypropyl-substituted chitosan derivatives of formula I are obtained, according to the invention, in that chitosan is reacted either in a two-step reaction, first with propylene oxide and then with an alkyl halide, or the two alkylating agents can act simultaneously, but at two different reaction temperatures.

The preferred process for producing the compounds of the general formula I is characterized in that a chitosan, consisting of 50 to 96% deacetylated chitin, is reacted in a first reaction step in the presence of an organic dispersing agent at a temperature of 20° C. to 120° C., preferably 80°-100° C., with propylene oxide and the hydroxypropylchitosan obtained is reacted in a second reaction step with an alkyl halide in alkaline medium at a reaction temperature of 40° to 120° C., preferably 60°-90° C.

The molar ratio of the chitosan to the alkylating agents is selected in each instance between 1:3 to 1:15.

In the simultaneous reaction of the chitosan with the two alkylating agents the reaction mixture is first stirred in the autoclave 3-60 hours at 20° to 120° C., preferably 12-48 hours at 20° to 40° C. Under these reaction conditions the N-hydroxypropylation preferably takes place. Next, the reaction mixture is stirred 3-60 hours at 40° to 120° C., preferably 6 to 24 hours at 60°-90° C., wherein the O-alkylation then elapses.

The excess alkyl halides which are contained as alkylating agents suffice as dispersing agents in both production methods insofar as the reaction temperature of the first reaction step is 20° to 40° C. At higher reaction temperatures additional organic dispersing agents such as, e.g., ethanol, isopropanol, dioxane, acetone and toluene, can be used.

The chlorides and bromides of straight-chain or branched alkanes with 1 to 6 carbon atoms are used as alkyl halides.

The working up of reaction mixtures is effected in that, after the excess propylene oxide is disposed of, the hydroxyalkylated intermediate product is isolated by means of concentrating from the organic solvent and, after the alkylation in alkaline medium, the excess alkali is removed by means of neutralization, respectively, the reaction mixture is concentrated and the chitosan derivative of formula I precipitates by means of pouring in distilled water.

The salts of the alkyl-hydroxypropyl-substituted chitosans of the general formula I, according to the invention, can be obtained, for example, by means of neutralization of the amino groups of the chitosan derivatives of formula I with acids. However, according to the present invention, only such salts as are soluble in water are usable. Suitable salts are, for example, those with hydrochloric acid, formic acid, acetic acid, lactic acid, glycolic acid, malonic acid, citric acid and adipic acid.

In contrast to synthetic polymers with finite residual monomer contents, the chitosan derivatives described above are physiologically harmless, biologically degradable and, in a manner analogous to the highly substituted, organosoluble, non-ionogenic cellulose ethers, can be used in adhesives and lacquers, pharmaceuticals and cosmetics and in foil and film production. In addition, the raw material, chitin, which is required for their production, is available in oceans as a constituent of crustaceans and lower plants in huge quantities, so that it seems sensible to turn to this raw material for industrial use for reasons of environmental protection as well as from economical viewpoints.

In particular, with the chitosan derivatives described above cosmetic agents for the treatment of hair or skin can be produced which are distinguished by surprisingly advantageous characteristics and which are characterized in that in a suitable cosmetic base they contain a macromolecular polymeric compound which is derived from chitosan derivatives and has the general formula I $$HO[C_6H_{11-m-q}NO_4(R^1)_m(R^2)_n(R^3)_q]_pH \qquad (I),$$

wherein m denotes any desired numerical value from 0 to 0.6, n denotes any desired numerical value from 0.5 to 10, q is a desired numerical value from 0.5 to 4, p denotes an integer from 50 to 5000, $R^1$ is an acetyl group, $R^2$ is a bivalent group

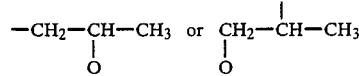

and $R^3$ denotes a straight-chain or branched alkyl group with 1 to 6 carbon atoms or its salt with an organic or inorganic acid.

The compositions containing chitosan derivatives of formula I, according to the invention, are suitable in general for the treatment of the skin and/or the hair. For example, they can be hair and/or body washing compositions, shading shampoos, hair creams, hair lotions, agents for strengthening the hair, washing lotions, hair drying lotions, hair treatments, anti-dandruff agents, agents for permanent hair shaping, agents for dyeing hair or removing dye, agents for application prior to or after hair coloring, and as cosmetic agents for care, protection or cleansing of the skin, such as face lotions, shaving lotions, moisturizing creams, cold creams, body lotions, sun protection compositions, or also makeup preparations such as cosmetic creams and rouges.

The contents of new chitosan derivatives of formula I in the cosmetic compositions described here is advisably 0.05 to 10 percent by weight, preferably 0.1 to 6.0 percent by weight.

The preferred subject matter of the present invention is a composition for strengthening the hair in the form of an alcoholic or aqueous-alcoholic solution of the chitosan derivative of formula I, wherein the chitosan derivative is preferably not in the form of salt. The compositions for strengthening the hair preferably contain the chitosan derivative in a quantity of 0.5 to 5 percent by weight.

In addition to the new chitosan derivative of formula I for the production of a cosmetic base, the cosmetic compositions, according to the present invention, can contain all those component parts which are normally used in hair and skin treatment compositions, particularly anionic, cationic, amphoteric, zwitter-ionic or non-ionic surface-active tensides, foam synergists, stabilizers, sequestering agents, pigments, thickeners, emulsifiers, buffer materials, preservatives, dyes, perfume oils, known cosmetic polymers, such as anionic, non-ionic, cationic or amphoteric polymers, natural substances, cosmetic oils, fat alcohols, waxes, foam stabilizers, active components againt dandruff, reducing agents and propellants.

In a preferred manner, the cosmetic compositions, according to the invention, have a pH value of 2 to 11 and can exist in the form of aqueous, alcoholic or aqueous alcoholic preparations, e.g. with an alcohol with 1 to 4 carbon atoms, as solutions, as creams, as gels, as dispersions or as emulsions. It is likewise possible to spray these compositions in the form of alcoholic or aqueous alcoholic solution by means of an atomizer or other suitable spraying devices or from a pressure vessel as aerosol hairspray in a mixture with conventional propellants which are liquified under pressure.

If the cosmetic compositions, according to the invention, are compositions for strengthening the hair, such as liquid hair fixers or hair sprays, they are usually in the form of alcoholic or aqueous alcoholic solutions which are characterized by a content of chitosan derivatives of the aforementioned formula I. In this case, the chitosan derivatives can be used alone as film forming or fixing resin. However, additionally known film forming natural or synthetic polymers can also be contained in the hair strengthening compositions according to the invention. For example, as natural polymers shellac, alginates, gelatins, pectins and cellulose derivatives come under consideration. Of the synthetic polymers the following can be used for example: polyvinyl pyrrolidone, polyvinyl acetate, polyacryl compounds, such as acrylic acid or methacrylic acid polymers, basic polymers of esters from acrylic acid or methacrylic acid with amino alcohols or the salts or quaternization products of these basic polymers, polyacrylonitrile, as well as co- or terpolymers from such compounds, for example, polyvinyl pyrrolidone-vinyl-acetate. The compositions then have a pH value between 6 and 8 in particular. Such compositions for strengthening hair normally contain film forming polymers in a total quantity of approximately 0.05 to 3.0 percent by weight. If the agents contain other film forming polymers in addition to the quaternary chitosan derivatives of formula I, the content of quaternary chitosan derivatives is correspondingly reduced.

In addition to alcohols, such as ethanol and isopropanol, ketones, such as acetone, halogenated hydrocarbons, such as for example, dichloro methane, as well as hydrocarbons and lower silicone oils, also come under consideration as solvents.

Since the new chitosan derivatives, according to the invention, are favorably soluble in organic solvents, insofar as they are not salts, they can also be used in anhydrous compositions for strengthening the hair.

When the compositions for strengthening the hair are in the form of aerosol preparations which are sprayed from a pressure vessel, they contain approximately 10 to 60 percent by weight of a propellant in the cosmetic base. Chlorfluoralkanes, such as, e.g. $CCl_3F$, $CCl_2F_2$, $C_2Cl_3F_3$, $CCl_2F-CCl_2F$, $CHCl_2F$, $CHClF_2$ and $CClF_2-CClF_2$, readily volatile hydrocarbons, such as, e.g. n-butane and n-propane, or dimethyl ether, $CO_2$, $N_2O$, $N_2$, $CH_2Cl_2$ and $CCl_3-CH_3$, can be used as propellant.

In addition, the compositions described here for strengthening the hair can contain the additives usual for such compositions, for example, modifiers, such as silicone oil, or softeners, such as isopropyl myristate, diethyl phthalate and diethyl stearate, as well as substances which improve combing ability.

The compositions for strengthening the hair, according to the invention, can, if necessary, color or shade the hair simultaneously by means of a content of cosmetic dyes. Such preparations are commercially known as color fixers or shading fixers. They contain dyes which are known and conventional for hair fortifiers, in addition, such as aromatic nitro dyes (e.g. 1,4-diamino-2-nitro-benzene), azo dyes (e.g. C.I. Acid Brown 4), anthraquinone dyes (e.g. C.I. Disperse Violet 4) and triphenylmethane dyes (e.g. C.I. Basic Violet 1), wherein the dyes of these classes can have acidic, non-ionogenic or basic character according to the type of their substituents. Their total concentration in these preparations is normally approximately 0.01 to 2.0 percent by weight.

The cosmetic compositions, according to the invention, in addition, can be compositions for strengthening hair without propellants. For this purpose, they are applied in liquid form to the hair prior to setting or drying.

The following examples explain the subject matter of the invention in more detail.

PRODUCTION EXAMPLES

Example 1

First step:
N-hydroxypropylation of chitosan 50 g (0.31 moles) chitosan ($\eta=140$ ml/g; free amine 86%; particle size $<25$ μm), together with 100 ml distilled $H_2O$, 100 ml ethanol and 209.08 g $\hat{=}$ 250 ml (3.6 moles) propylene oxide, are put into an autoclave and stirred for 12 hours at 100° C.

After the reaction is finished, the highly viscous, brown substance is diluted with a mixture of ethanol/$H_2O$ 1:1, the solution is brought to a boil briefly under the hood in order to remove propylene oxide residue which might possibly remain and, in case clarification is necessary, a pressure filtration is carried out prior to concentration in the rotation evaporator.

It is first dried in the atmosphere, then at 50° C. in the vacuum drying cabinet, and a hydroxypropylchitosan is obtained in a yield of 92% of theoretical, assuming successful disubstitution.

Characteristic data of the reaction product:
limiting viscosity number: $[\eta]_{THF}^{25°\,C.}=49$ ml/g (measured in aqueous 0.2 m acetic acid/0.1 m sodium acetate solution)

substitution degree hydroxypropyl (n): 1.70
substitution degree acetyl (m): 0.22

Second step:
O-ethylalkylation of N-hydroxypropyl-chitosan 83.1 g (0.3 moles) of the N-hydroxypropyl-chitosan from the preceding reaction are introduced into an autoclave together with 40 ml 43% NaOH, 400 ml acetone and 327.0 g $\hat{=}$ 225 ml (3.0 moles) ethyl bromide and stirred for 12 hours.

After the reaction is finished, the viscous, slightly yellow solution is adjusted to pH 7 by means of concentrated HCl, concentrated until dry with the rotation evaporator and the main portion of the inorganic by-products is separated by means of absorption in absolute ethanol.

The ethanolic filtrate is added accompanied by intensive stirring in distilled water, the precipitate is collected, it is washed so as to be halide free and is dried at 50° C. in the vacuum drying cabinet.

For additional purification the isolated product can be dissolved in 2 l methylene chloride, dried over $CaCl_2$, the solution is pressure filtrated and, after concentration, can be dried in the atmosphere or at 50° C. in the vacuum drying cabinet.

The resulting transparent, highly glossy polymer film is broken up into small pieces in a cross beater mill. The chitosan derivative obtained in this way has the following characteristic data:

limiting viscosity number: $[\eta]_{THF}^{25°\ C.} = 33$ ml/g
substitution degree ethyl (q): 2.30
substitution degree hydroxypropyl (n): 1.70
substitution degree acetyl (m): 0.22

Example 2

O-butylalkylation of N-hydroxypropyl-chitosan 50 g (0.181 moles) of the N-hydroxypropyl-chitosan obtained from the first step in Example 1 are put into an autoclave together with 80.8 ml 43% NaOH, 235 ml acetone and 248 g ≙ 195 ml (1.81 moles) 1-brombutane and are stirred for 24 hours at 90° C.

The working up and isolation is effected in the manner described for the second step in Example 1.

Characteristic data of the chitosan derivative:
limiting viscosity number: $[\eta]_{THF}^{25°\ C.} = 22$ ml/g
substitution degree butyl (q): 3.54
substitution degree hydroxypropyl (n): 1.70
substitution degree acetyl (m): 0.22

Example 3

O-hexylalkylation of N-hydroxypropyl-chitosan 50 g (0.181 moles) of the N-hydroxypropyl-chitosan produced according to Example 1 are put into an autoclave together with 80.8 ml 43% NaOH, 235 ml acetone and 109.16 ≙ 95 ml (0.905 moles) 1-chlorhexane and stirred for 18 hours at 90° C.

After working up and isolation, as described in Example 1, a transparent, soft, flexible mixed ether derivative of chitosan is obtained.

Characteristic data of the chitosan derivative:
limiting viscosity number: $[\eta]_{THF}^{25°\ C.} = 14$ ml/g
substitution degree hexyl (q): 1.46
substitution degree hydroxypropyl (n): 1.70
substitution degree acetyl (m): 0.22

Example 4

Simultaneous reaction of the chitosan with propylene oxide and an alkyl halide (ethyl chloride)

20 g (0.12 moles) chitosan ($\eta = 140$ ml/g; free amine 86%; particle size < 25 μm) are added with 325 ml 43% NaOH, converted into alkali chitosan by means of triple freezing for 30 minutes and subsequent thawing for 60 minutes.

The alkali chitosan is suctioned until a wet weight of 160-165 g is reached, introduced together with 174.2 g ≙ 210 ml (3.0 moles) propylene oxide and 193.6 g ≙ 211 ml (3.0 moles) ethyl chloride in an autoclave and the mixture is allowed to react first for 12 hours at 35° C. and then for another 12 hours at 90° C. accompanied by stirring. After the reaction is finished, the viscous solution is diluted with a mixture of acetone and $H_2O$, the excess, unreacted alkylating agents are removed and an adjustment to pH 7 is made by means of concentrated HCl. The main quantity of inorganic salt is separated by means of concentrating until dry and subsequent absorption in acetone. The acetonic filtrate is added in distilled $H_2O$, accompanied by intensive stirring, the precipitate is collected, it is washed so as to be halide free and dried at 50° C. in the vacuum drying cabinet.

The obtained chitosan derivative has the following characteristic numbers:

limiting viscosity number: $[\eta]_{THF}^{25°\ C.} = 44$ ml/g
substitution degree hydroxypropyl (n): 1.76
substitution degree ethyl (m): 2.40

The substitution degree for the hydroxypropyl- and alkyl groups was determined in each instance by means of the $^1$H-NMR spectra.

EXAMPLES FOR COSMETIC COMPOSITIONS

Examples 5-17 are aerosol hairsprays. In all cases hairsprays were obtained with excellent characteristics with respect to application technology which, in comparison to commercially available hairsprays in particular, effect a more natural feel of the hair, a shorter drying time and a more natural appearance of the hair.

Examples 18-28 show the possibility for the combined use of the chitosan derivatives, according to the invention, with known commercially available hairspray resins for aerosol hairsprays. In all cases hairsprays were obtained with good characteristics with respect to application technology, which, in comparison to commercially available hairsprays, have easier combing ability and hairstyling ability which is improved because of lower electrostatic charge.

Examples 29-34 show the use of the cosmetic compositions, according to the invention, as non-aerosol hairsprays, that is, compositions for strengthening the hair without propellants which are intended for application on the hair by means of a spray pump. In all recipes a good hold of the hair is obtained with natural feel and appearance after use.

Examples 35 and 36 show the use of the compositions, according to the invention, as hair setting compositions. 15 ml of the hair setting compositions are applied and distributed on the hair prior to curling. After setting and drying a good hold of the hairstyle obtained is achieved.

| | Examples 5-17: Aerosol hairsprays (all data in percent by weight) | | | | | | | | | | | | |
|---|---|---|---|---|---|---|---|---|---|---|---|---|---|
| Example No. | 5 | 6 | 7 | 8 | 9 | 10 | 11 | 12 | 13 | 14 | 15 | 16 | 17 |
| Chitosan derivative according to Ex. 1 | 2.65 | 2.65 | 2.65 | 2.65 | 2.65 | 2.65 | 2.65 | 2.65 | 2.65 | 2.65 | 2.65 | 2.65 | 2.65 |
| perfume oil | 0.18 | 0.18 | 0.18 | 0.18 | 0.18 | 0.18 | 0.18 | 0.18 | 0.18 | 0.18 | 0.18 | 0.18 | 0.18 |
| silicone oil | 0.04 | 0.04 | 0.04 | 0.04 | 0.04 | 0.04 | 0.04 | 0.04 | 0.04 | 0.04 | 0.04 | 0.04 | 0.04 |
| isopropanol | 57.13 | 22.13 | — | — | 57.13 | 22.13 | — | — | 12.14 | — | 12.14 | — | 12.14 |
| methylene chloride | — | 35.00 | — | 35.00 | — | 35.00 | — | 35.00 | 35.00 | 35.00 | 35.00 | 35.00 | 35.00 |

-continued

| | | | | | | | | | | | | |
|---|---|---|---|---|---|---|---|---|---|---|---|---|
| ethanol | — | — | 57.13 | 22.13 | — | — | 57.13 | 22.13 | — | 12.14 | — | 12.14 | — |
| acetone | — | — | — | — | — | — | — | — | 9.99 | 9.99 | 9.99 | 9.99 | 9.99 |
| total Propellants | 60.00 | 60.00 | 60.00 | 60.00 | 60.00 | 60.00 | 60.00 | 60.00 | 60.00 | 60.00 | 60.00 | 60.00 | 60.00 |
| 50:50 mixture of $CCl_3F$ and $CCl_2F_2$ | 40.00 | 40.00 | 40.00 | 40.00 | — | — | — | — | 40.00 | 40.00 | — | — | — |
| mixture of propane/butane in ratio of 80:20 | — | — | — | — | 40.00 | 40.00 | 40.00 | 40.00 | — | — | 40.00 | 40.00 | 20.00 |
| $CCl_3F$ | — | — | — | — | — | — | — | — | — | — | — | — | 20.00 |
| | 100.00 | 100.00 | 100.00 | 100.00 | 100.00 | 100.00 | 100.00 | 100.00 | 100.00 | 100.00 | 100.00 | 100.00 | 100.00 |

Examples 18–28: Aerosol hairsprays with resin mixtures (all data in percent by weight)

| Example no. | 18 | 19 | 20 | 21 | 22 | 23 | 24 | 25 | 26 | 27 | 28 |
|---|---|---|---|---|---|---|---|---|---|---|---|
| Chitosan derivative according to Example 2 | 2.50 | 2.50 | 2.50 | 2.50 | 2.50 | 1.50 | 1.50 | 1.50 | 1.50 | 1.50 | 1.50 |
| copolymer from vinylpyrrolidone/vinyl acetate (30:70), 50% isopropanolic solution | 0.50 | — | — | 0.50 | 0.50 | 1.50 | — | — | — | 1.50 | 1.50 |
| copolymer from vinylpyrrolidone/vinyl acetate (30:70) 50% ethanolic solution | — | — | — | — | — | — | 1.50 | — | — | — | — |
| copolymer from vinyl acetate/crotonic acid (90:10) solid | — | 0.50 | — | — | — | — | — | 1.50 | — | — | — |
| copolymer from octylacrylamide/acrylic acid/butylaminoethylmethacrylate, solid (AMPHOMER ® of National Starch Chem. Corp. U.S.A.) | — | — | 0.50 | — | — | — | — | — | 1.50 | — | — |
| perfume oil | 0.18 | 0.18 | 0.18 | 0.18 | 0.18 | 0.18 | 0.18 | 0.18 | 0.18 | 0.18 | 0.18 |
| silicone oil | 0.04 | 0.04 | 0.04 | 0.04 | 0.04 | 0.04 | 0.04 | 0.04 | 0.04 | 0.04 | 0.04 |
| isopropanol or ethanol | 56.78 | 56.78 | 56.78 | 21.78 | 11.78 | 56.78 | 56.78 | 56.78 | 56.78 | 21.78 | 11.78 |
| methylene chloride | — | — | — | 35.00 | 35.00 | — | — | — | — | 35.00 | 35.00 |
| acetone | — | — | — | — | 10.00 | — | — | — | — | — | 10.00 |
| 50:50 mixture of $CCl_3F$ and $CCl_2F_2$ | — | — | — | — | — | 40 | 40 | 40 | 40 | 40 | 40 |
| mixture of propane and butane in the ratio of 80:20 | 40 | 40 | 40 | 40 | 40 | — | — | — | — | — | — |
| | 100.0 | 100.0 | 100.0 | 100.0 | 100.0 | 100.0 | 100.0 | 100.0 | 100.0 | 100.0 | 100.0 |

Examples 29–34: Non-aerosol hairsprays (hairsprays without propellant gas) (all data in percent by weight)

| Example no. | 29 | 30 | 31 | 32 | 33 | 34 |
|---|---|---|---|---|---|---|
| chitosan derivative according to Example 1 | 3.00 | 3.00 | 3.00 | — | — | — |
| chitosan derivative according to Example 4 | — | — | — | 2.50 | 0.50 | 2.50 |
| copolymer of vinylpyrrolidone vinylacetate (30:70), 50% alcoholic solution | — | — | — | 0.50 | 2.50 | 0.50 |
| silicone oil | 0.05 | 0.05 | 0.05 | 0.05 | 0.05 | 0.05 |
| isopropanol | 60.00 | — | 40.00 | 60.00 | — | 40.00 |
| ethanol | — | 60.00 | — | — | 60.00 | — |
| acetone | — | — | 20.00 | — | — | 20.00 |
| perfume oil | 0.20 | 0.20 | 0.20 | 0.20 | 0.20 | 0.20 |
| water | 36.75 | 36.75 | 36.75 | 36.75 | 36.75 | 36.75 |
| | 100.00 | 100.00 | 100.00 | 100.00 | 100.00 | 100.00 |

Examples 35 and 36: Hair setting compositions (all data in percent by weight)

| Example no. | 35 | 36 |
|---|---|---|
| chitosan derivative according to Example 1 | 2.88 | 1.44 |
| copolymer of vinylacetate/crotonic acid/ethylene oxide, 60% isopropanolic solution (CAS no. 25 609-89-6) | — | 4.80 |
| isopropanol | 2.60 | 2.60 |
| ethanol | 45.00 | 45.00 |
| perfume oil | 0.40 | 0.40 |
| diethyl phthalate | 0.20 | 0.20 |
| water | 48.92 | 45.56 |
| | 100.00 | 100.00 |

We claim:

1. Cosmetic composition for the treatment of hair or skin, characterized in that it contains in a suitable cosmetic base a macromolecular, polymeric compound, derived from chitosan, of the general formula (I)

$$HO[C_6H_{11-m-q}NO_4(R^1)_m(R^2)_n(R^3)_q]_pH \quad (I),$$

wherein m denotes a numerical value from 0 to 0.6, n denotes a numerical value from 0.5 to 10, q is a numerical value from 0.5 to 4, p denotes an integer from 50 to 5000, $R^1$ is an acetyl group, $R^2$ is a bivalent group

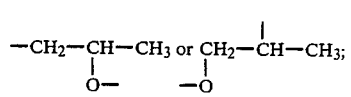

and $R^3$ denotes a straight-chain or branched alkyl group with 1 to 6 carbon atoms, or its salt with an organic or inorganic acid.

2. Composition according to claim 1, characterized in that n in formula (I) denotes a numerical value from 1 to 3.

3. Composition according to claim 1, characterized in that q in formula (I) denotes a numerical value from 1 to 3.6.

4. Composition according to claim 2, characterized in that q in formula (I) denotes a numerical value from 1 to 3.6.

5. Composition according to claim 1, characterized in that it contains said polymeric compound of formula (I) in a quantity of 0.05 to 10 percent by weight.

6. Composition according to claim 1, characterized in that said cosmetic base is an aqueous, alcoholic or aqueous-alcoholic solution, a cream, a gel or an emulsion.

7. Composition according to claim 1, characterized in that it comprises, as cosmetic base, an alcoholic or aqueous-alcoholic solution of ethanol or isopropanol, has a pH value between 6 and 8 and is a composition for strengthening the hair.

8. Composition according to claim 1, characterized in that said cosmetic base is an alcoholic or aqueous-alcoholic solution which is mixed with a propellant gas, which is liquified under pressure, bottled in a pressure vessel and is in the form of an aerosol hairspray.

9. Composition according to claim 1, characterized in that it contains, in addition, a film-forming synthetic or natural cosmetic polymer.

10. Composition according to claim 1, characterized in that said cosmetic base is an aqueous, alcoholic or aqueous-alcoholic solution, a gel or an emulsion which contains, in addition, a dye and is in the form of a color fixer or shading fixer.

11. Macromolecular polymeric compound which is derived from chitosan and has the general formula (I)

$$HO[C_6H_{11-m-q}NO_4(R^1)_m(R^2)_n(R^3)_q]_pH \qquad (I),$$

wherein m denotes a numerical value from 0 to 0.6, n denotes a numerical value from 0.5 to 10, q is a numerical value from 0.5 to 4, p denotes an integer from 50 to 5000, $R^1$ is an acetyl group, $R^2$ is a bivalent group

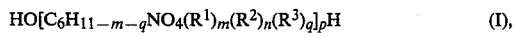

and $R^3$ denotes a straight-chain or branched alkyl group with 1 to 6 carbon atoms, or its salt with an organic or inorganic acid.

12. Compound according to claim 11, characterized in that in said formula (I) n denotes a numerical value from 1 to 3, q is a numerical value from 1 to 3.6 and the limiting viscosity number has a value from 14 to 44 mL/g.

13. Compound according to claim 11, constructed from 4 to 50 mole % units of the general formula

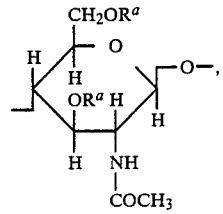

40 to 96 mole % units of the general formula

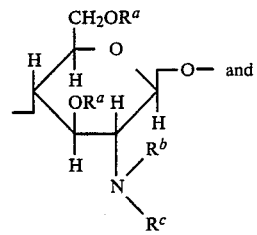

0 to 10 mole % units of the general formula

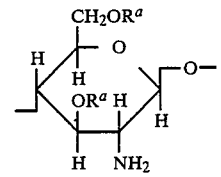

in random distribution, wherein $R^a$ denotes H or $C_1$-$C_6$-alkyl, $R^b$ is H or

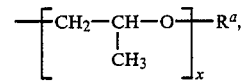

with x being equal to an integer from 1 to 5, and $R^c$ denotes

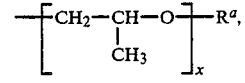

assuming that at least one of the substituents $R^a$ in formula A or B denotes $C_1$-$C_6$-alkyl.

14. Process for producing the compounds according to claim 11, characterized in that a chitosan, consisting of 50 to 90% deacetylated chitin, is reacted in a first reaction step in the presence of an organic dispersing agent at a temperature of 20° C. to 120° C. with propylene oxide, and the obtained N-hydroxypropyl-chitosan is made to react in a second reaction step with an alkyl halide in an alkaline medium at a reaction temperature of 40° C. to 120° C.

* * * * *